United States Patent [19]

McGowan et al.

[11] Patent Number: 4,974,455

[45] Date of Patent: Dec. 4, 1990

[54] DILUTION EXTRACTIVE PROBE

[75] Inventors: Gerald F. McGowan, Parker; Ronald L. Ketchum, Littleton, both of Colo.

[73] Assignee: Lear Siegler Measurement Controls Corporation, Englewood, Colo.

[21] Appl. No.: 400,462

[22] Filed: Aug. 29, 1989

[51] Int. Cl.[5] .............................................. G01N 1/24
[52] U.S. Cl. ......................... 73/863.120; 73/863.230; 73/863.810
[58] Field of Search ........... 73/863.12, 863.11, 863.23, 73/863.81, 28, 23, 864.81

[56] References Cited

U.S. PATENT DOCUMENTS

| | | | |
|---|---|---|---|
| 4,004,882 | 1/1977 | Byrne et al. | 73/863.12 X |
| 4,154,088 | 5/1979 | Werner | 73/863.12 X |
| 4,161,883 | 7/1979 | Laird et al. | 73/863.81 X |
| 4,484,481 | 11/1984 | Laird et al. | 73/863.12 |
| 4,856,352 | 8/1989 | Daum et al. | 73/863.12 X |

OTHER PUBLICATIONS

Lear Siegler Measurement Controls Corp.-TRS Extractive System, Feb. 1988.
Lear Siegler Measurement Controls Corp.-Extractive Monitoring System, Jun. 1988.
Lear Siegler Measurement Controls Corp.-Dynatron 5000, Sep. 1988.

Primary Examiner—Hezron E. Williams
Assistant Examiner—Joseph W. Roskos
Attorney, Agent, or Firm—Fields, Lewis, Pittenger & Rost

[57] ABSTRACT

A dilution extractive probe assembly for sampling a gas stream in a stack is provided. It includes a hollow tubular dilution probe having a first end for receiving a sample of the gas stream from the stack to be analyzed and a second end through which the sample is discharged after dilution. A first filter is provided at the first end of the probe for filtering the sample gas it passes into the probe. A critical orifice is located within the probe downstream of the first filter. A first heater is provided for heating the first filter to maintain the sample at a temperature above the dew point of the sample gas. A partial vacuum is created for drawing the sample through the filter and into the probe. An eductor is located adjacent the second end of the probe for mixing the sample with a dilution gas. A second heater for heating the eductor to maintain the sample gas at a temperature above its dew point as it passes through the eductor is provided.

13 Claims, 3 Drawing Sheets

Fig_1

DILUTION EXTRACTIVE PROBE

TECHNICAL FIELD

This invention relates to a dilution probe for sampling a gas stream in a stack and more particularly to such a probe having spaced heaters to maintain the gas above the dew point as it passes through the probe from a first end to a second end.

BACKGROUND ART

As the requirements for controlling pollution from smoke stacks become more stringent, it is important that suitable monitoring equipment be provided to measure the extent and composition of particulate matter and gases from these stacks. These stack gases are often "dirty" and "wet", i.e., they are laden with particulate material and have very high moisture content, all of which tends to damage or clog the measuring equipment. This often results in breakdown of the equipment and/or in faulty readings. The cost of maintenance and repair and down time can be excessive.

One prior art gas sampling device is an extractive probe manufactured and sold by Lear Siegler Measurement Controls Corporation of Englewood, Colo., Model No. 80280366. The extractive probe is mounted on the sidewall of a stack. It has a probe which extends in toward the center of the stack and an external filter outwardly of the stack and in fluid communication with the probe. A flange is provided which attaches the device to the sidewall. The filter is in fluid communication with a vacuum pump which draws gas from the stack through the probe and the filter so that it may be supplied to an analyzer which measures the level of a particular gas under surveillance, such as $SO_2$. The filter separates out any particulate material that may be in the gas stream in the stack so that it does not pass through the pump or into the analyzer. A typical filter is porous having many small openings. As a result, the gas increases in velocity as it passes through these openings in the filter. As this happens, the gas pressure drops and if the gas is wet, the moisture may exceed the dew point and condense out into the filter, thereby clogging it. To minimize this possibility, the filter is heated. Also, the lines through which the sample gas passes are also heated. While this equipment generally works well for its intended purpose, the heating of the sample lines is expensive and increases the maintenance requirements.

Another prior art device is a dilution probe extractive system sold by Lear Siegler Measurement Controls Corporation of Englewood, Colo. under the trademark "Dynatron 5000", which has particular application in measuring $SO_2$, $NO$, $NO_2$, $NO_x$, $CO$, $CO_2$ and $HCL$. This device includes a probe which is mounted on the sidewall of a stack as described above. The sample gas is drawn through a filter to remove particulates from the sample before the gas reaches a critical orifice provided within the probe. The flow of the gas through the critical orifice is at sonic velocities. The gas then passes through a primary nozzle where it is mixed with a dilution gas. The diluted gas passes through an eductor at sonic velocity and is supplied to an analyzer. This technique allows a fairly constant flow rate of gas through the probe over a wide range of external process temperatures and pressure variations. Since no water is removed from the diluted sample process stream, measurements are on a volumetric, wet basis. However, when the gas moves at sonic velocities the pressure drops and if the gas is wet the moisture may condense out and clog the critical orifice thereby impeding the operation and efficiency of the dilution probe.

DISCLOSURE OF THE INVENTION

In accordance with this invention a dilution extractive probe assembly for sampling a gas stream in a stack is provided. It includes a hollow tubular dilution probe having a first end for receiving a sample of the gas stream from the stack to be analyzed and a second end through which the sample is discharged after dilution. A first filter is provided at the first end of the probe for filtering the sample gas as it passes into the probe. A critical orifice is located within the probe downstream of the first filter. A first heater is provided for heating the first filter to maintain the sample at a temperature above the dew point of the sample gas. Means is provided for drawing the sample through the filter and into the probe. An eductor is located adjacent the second end of the probe for mixing the sample with a dilution gas. A second heater for heating the eductor to maintain the sample gas at a temperature above its dew point as it passes through the eductor is provided.

A second cylindrical filter of slightly greater diameter than the probe is provided which has a closed end and an open end and is positioned over the first end of the probe, but spaced therefrom. The second filter may be made of sintered metal and the first heater surrounds the second filter. A first protective shroud can be provided around the second filter and the first heater. A stack probe extends from the first end of the dilution probe and is positionable in a stack through which the stack gas to be sampled passes. A flange connected to the stack probe attaches the probe assembly to the stack.

The invention also includes means for sensing the sample gas pressure in the dilution probe. Additionally, means is provided for sensing the pressure in the eductor and a dilution control panel is provided for sensing and regulating the sample gas pressure and the eductor pressure. In addition, a first temperature sensing means is positioned to sense the temperature of the sample at the second filter. A second temperature sensing means is positioned to sense the temperature of the sample at the eductor and a heater controller assembly is connected to the first and second heaters and the first and second temperature sensing means to control the respective heaters in response to the temperatures sensed by the respective temperature sensing means.

The sample drawing means may include a second eductor through which a gas flows. The second eductor is in fluid communication with the space between the second filter and the first end of the probe so that the low pressure created by the gas passing through the second eductor draws the sample gas through the second filter into the probe and into the second eductor. A fluid line can be provided which is connected between the second eductor and the stack to convey the gases from the second eductor back to the stack. Conveniently, the gas provided to the second eductor can be the dilution gas.

A second protective cylindrical shroud can extend around the remainder of the probe and be attached to the second end thereof. A third cylindrical shroud can be attached and extend from the second shroud to protect the fluid and electrical lines connected to the probe.

With the invention just described, it is possible to provide a highly effective dilution extraction probe wherein a wet, dirty gas can be sampled with minimal deleterious effects on the probe. The filters will filter out the particulate material. Also, as designed, the gas passes through the filter, the critical orifice and through the first eductor which combines the dilution gas with the sample gas at sonic speeds. This causes the pressure of the gas passing through the probe to drop and its temperature to be lowered. However, by providing two heaters, a first one around the filter and the second one around the eductor which combines the dilution gas with the sample gas, the temperature of the gas passing through the probe can be kept above the dew point of the sample gas as it passes from the upstream end of the probe to the downstream end thereof. With this arrangement the possibility of the moisture in the gas condensing out within the filters or the critical orifice is minimized.

Additional advantages of this invention will become apparent from the description which follows, taken in conjunction with the accompanying drawings.

BEST MODE FOR CARRYING OUT THE INVENTION

Figure 1:
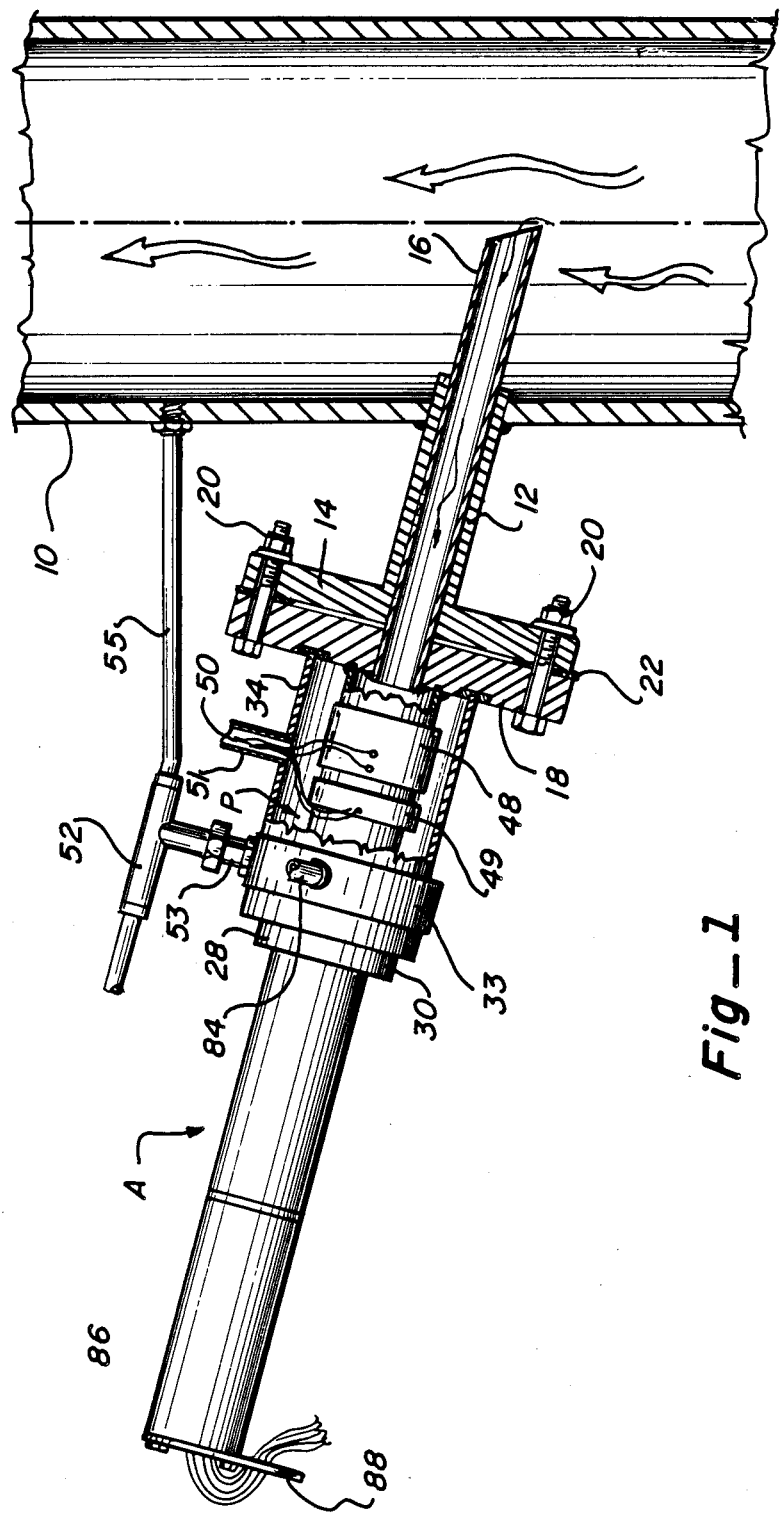
FIG. 1 is a side elevation of the dilution extractive probe constructed in accordance with this invention, partially in section, installed in a stack.
Figure 2:
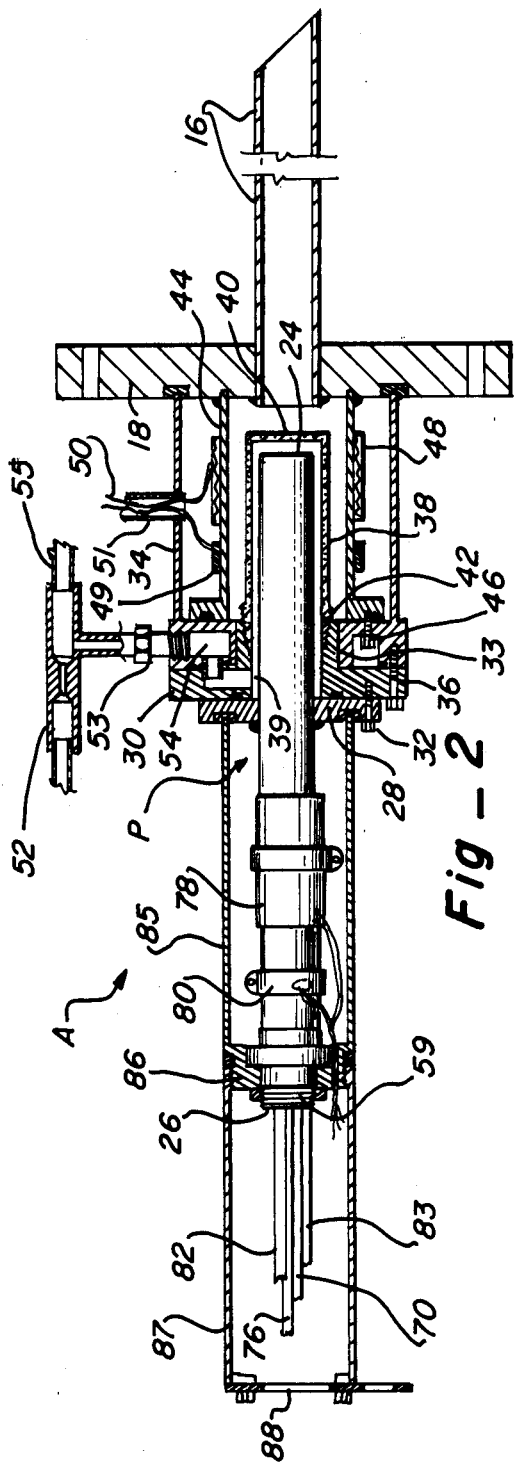
FIG. 2 is an enlarged longitudinal section of the dilution extractive probe of FIG. 1 showing additional details thereof.

In accordance with this invention a dilution probe assembly A is mounted in a stack 10, as shown in FIG. 1. This dilution probe is designed to measure gases at temperatures up to 200° C. Conveniently, the stack has a cylindrical probe mount 12 mounted at an incline to the stack, as shown, which has a peripheral mounting flange 14. The dilution probe assembly has a stack probe 16 which is slidable through probe mount 12 and into the stack, as shown. A flange 18 is provided at the proximate or downstream end of stack probe 16 and is attached to flange 14, as by bolts 20, with a sealing gasket 22 therebetween. Mounted centrally of dilution probe assembly A is gas sampling probe P. A suitable probe for this purpose is Model No. 0797.303, manufactured by EPM Environmental & Process Monitoring, Dalerstraat 32, 7843 PE ERM, The Netherlands. Referring to FIG. 2, this probe has an inlet end 24 through which the sample gas is drawn, as will be described more fully below. The gas passes through the center of the probe and is mixed with a dilution gas to form a diluted gas that is conveyed by a conduit which passes out the second downstream end 26. Probe P is mounted intermediate its ends 24 and 26 in a support flange 28. Conveniently, support flange 28 is attached to end plate 30 by bolts 32. End plate 30 is connected to end cap 33 on housing or end plate 30, as by bolts 36. The shroud 34 protects the portions of dilution probe assembly contained therein from rain and other natural elements. The forward end of shroud 34 is attached to flange 18, as shown.

A cylindrical filter 38 has a closed end 40 and a threaded end 42 which threadably attaches it to end plate 30, as shown. As seen, filter 38 completely encloses the upstream and portion of gas sampling probe P, but is spaced therefrom in all directions to provide a space 39 therebetween. A suitable sintered filter is Model No. 2224-B06-04-A00-5-AB or Model No. 2224-B06-04-A00-2-LB manufactured by Mott Metalurgical Corporation, Farmington Industrial Park, Farmington, Conn. 06032. A sleeve 44 surrounds filter 38, as shown, and is attached at its upstream end to flange 18, as by welding, and at its downstream end to housing 34, as by bolts 46. Conveniently, a heater 48 extends around sleeve 44 for heating the sample gas drawn through the filter and into gas sampling probe P. In addition, a thermocouple 49 or other heat sensing means is provided around sleeve 44 for sensing the temperature of the sleeve for regulating heater 48. The electrical wires 50 for the heater and thermocouple extend through a conduit 51 which is mounted on housing 34. The heater may be any suitable size, but a 100–300 watt heater has been found to be satisfactory.

Conveniently, an eductor 52 is connected by means of a fitting 53 to end cap 33. Within end cap 33 is another fitting 54 in fluid communication with fitting 53 and in fluid communication with the space between probe P and filter 38. Thus, as air passes through eductor 52, it will create a partial vacuum drawing the sample gas from the stack into the probe, a portion of this gas being passed out through eductor 52 and back to the stack by means of conduit 55.

Figure 3:
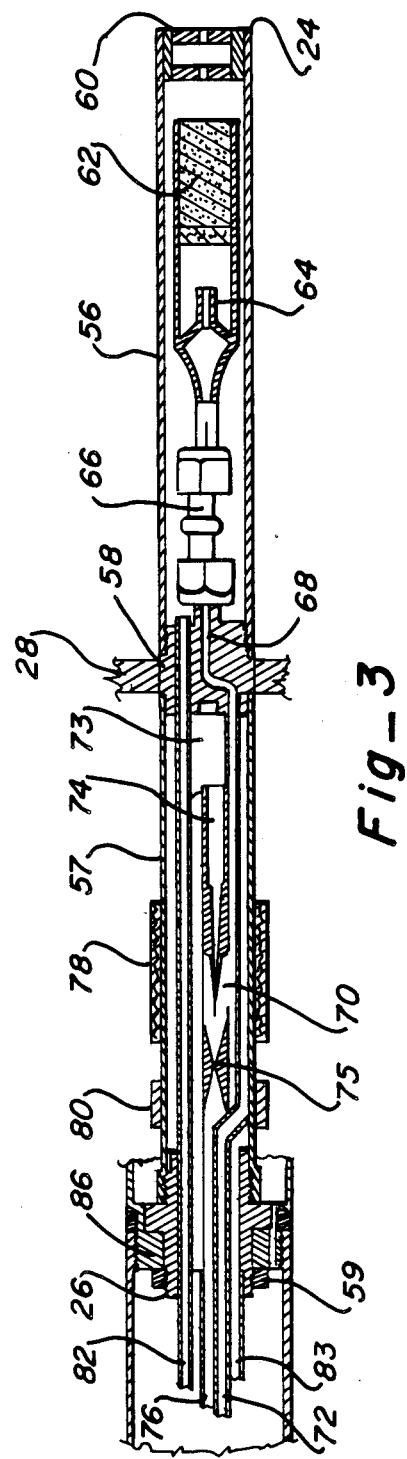
FIG. 3 is a horizontal section of the probe showing the internal construction thereof.

Turning to FIG. 3, the gas sampling probe includes an upstream housing 56 axially aligned and connected to a downstream housing 57 by a connector 58. A conduit support 59 is provided at the downstream end 26 of housing 57, as shown. At the upstream end 24 of housing 56, stack gas is first drawn through a course filter 60 and then through a fine filter 62, after which it passes through a critical orifice 64 which brings the stream of gas to sonic velocity. The critical orifice can be chosen from Model Nos. 2126.49 through 2126.64, manufactured by EPM Environmental & Process Monitoring, depending on the dilution rate required. Although the gas is expanding and dropping in pressure, because of the presence of heater 48, previously described, the temperature of the gas can be maintained above the dew point so that it does not condense either in the filters or in the critical orifice and plug them up. After passing critical orifice 64, the stack gas passes through a fitting 66 and a passageway 68 to a primary nozzle 70. At nozzle 70, the stack gas is mixed with a dilution gas. The dilution gas enters the downstream end of probe P through passageway 72 to chamber 73. The dilution gas is then drawn through passageway 74 into primary nozzle 70 and through eductor 75. The stack gas and dilution gas are thoroughly mixed in the primary nozzle and pass through eductor 75 at sonic speed. This permits the maintenance of a relatively constant pressure and flow of gas from critical orifice 64 to eductor 75 over a wide range of exterior pressure and temperature conditions. After passing eductor 75 the gas passes through conduit 76 to an analyzer, discussed below. In order to maintain the sample gas at the appropriate temperature as it passes through the primary nozzle and the eductor, a heater 78 is provided which extends around the downstream housing 57. A thermocouple 80 also extends around downstream housing 57 adjacent heater 78 and senses the temperature at this location for controlling the heater 78. This heater also can be in the 100-300 watt size.

All of the conduits and passageways are supported in conduit support 59. A calibration line/zero gas passageway 82 also extends through the conduit support 59 and through connector 58 into the area within housing 56 adjacent fitting 66. In order to calibrate the probe P, gas can be provided through conduit 82 under pressure sufficient to fill housing 56 and force gas out through course filter 60 and into the gas stack. In other words, the entire housing 56 can be purged of sample gas. Initially, a "zero gas" can be used for this purpose. This is a gas which is completely free of the particular gas being measured. By this means, the probe will provide a signal to the analyzer which can be used as a zero value. Next, a gas of a known concentration of the gas to be measured is introduced through passageway 82 and a second reading is made by the analyzer. Based on these two values, any other value read when stack gas is introduced can be correlated to provide an accurate reading of the contaminates or gases under observation within the stack gas. Finally, a conduit 83 extends through conduit support 59 to a vacuum gauge (not shown) for measuring the pressure within the probe P.

An alternative line can be provided for purging and calibration which is more efficient than purging through passageway 82. The calibration line/zero gas can be introduced through conduit 84 which passes through end cap 33, as shown in FIG. 1, and communicates with space 39, shown in FIG. 2. Conduit 84 allows a greater and faster flow of gas. The calibration is accomplished in the same manner as previously described.

As shown in FIG. 2, an upstream probe housing 85 has a downstream end attached to support flange 28 and a downstream, externally threaded probe support 86. A downstream conduit housing 87 has one end attached to the threaded portion of support 86 which protects the conduits and guides them through conduit bracket 88 at the other end which holds the conduits, as best seen in FIG. 1 so that they do not kink as they go from the probe to the various instruments and controls, best shown in FIG. 4.

Figure 4:
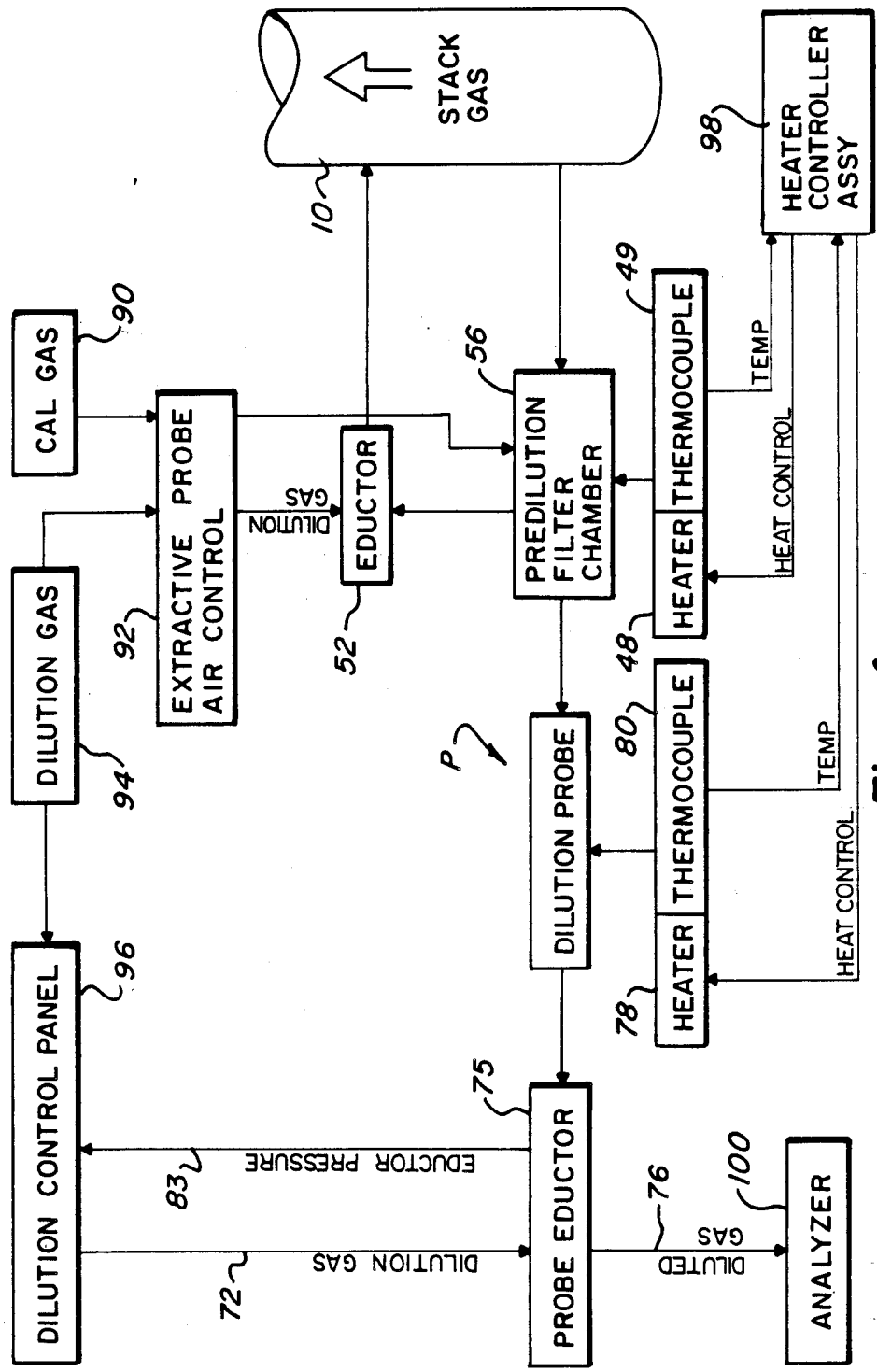
FIG. 4 is a flow diagram showing the overall operation of the probe and associated equipment.

FIG. 4 is a flow diagram showing the overall arrangement of controls as they relate to the dilution probe assembly A of this invention. The calibration gas can supplied from a supply 90 to an extractive probe air control 92 where it is supplied to the predilution filter chamber 56. The extractive probe air control can also regulate the flow of dilution gas from a supply 94 to eductor 52. The dilution gas is also supplied to dilution control panel 96. The dilution control panel supplies the dilution gas to the probe eductor 75, as previously described. It will also sense eductor pressure from eductor 75 through line 83. The heaters and the thermocouples are respectively connected to heater control assembly 98, as shown to properly regulate the heaters to control the temperature within the probe P. The diluted gas passes through an analyzer 100 which provides a readout of the concentration of the particular gas being analyzed. Calibration gas 98 from source 90 is provided which passes through extractive probe air controller 92, the predilution filter chamber 56, as previously described, for the purpose of setting values for use in the analyzer for determining the parts per million of the measured gas. As can be seen, the dilution gas from dilution gas source 90 can be used both for diluting the stack gas and as a gas for passing through eductor 52 for creating a vacuum for drawing the stack gas into the probe for sampling.

From the foregoing, the advantages of this invention are readily apparent. A dilution extractive probe has been provided wherein the gas stream within the probe is maintained at substantially constant temperature and pressure over wide variations in external temperature and pressure. This is accomplished by providing a first heater around the filter at the upstream end of the probe and providing a second heater at the downstream end near the eductor. With this unique arrangement, the temperature of the stack gas through the probe is always maintained above the dew point so that even when very wet gases are used they do not condense within the device and therefore do not plug up the filters or the critical orifice. As a result, the device is much more effective and requires less maintenance than heretofore possible. Also, more accurate readings are obtainable. Furthermore, the filtering means allows the device to be used with very dirty gases but because condensation can be minimized the chance of the filter unduly plugging up is greatly reduced.

This invention has been described in detail with reference to a particular embodiment thereof, but it will be understood that various other modifications can be effected within the spirit and scope of this invention.

What is claimed is:

1. A dilution extractive probe assembly for sampling a gas stream in a stack, said assembly comprising:
   a hollow tubular dilution probe having a first end for receiving a sample of the gas stream from the stack to be analyzed and a second end through which the sample is discharged after dilution;
   a first filter at said first end of said probe for filtering the sample gas as it passes into said probe;
   a critical orifice within said probe downstream of said first filter through which the sample gas passes at sonic speed;
   a first heater for heating the sample gas to maintain it above its dew point as it passes into said probe;
   means for drawing the sample through said first filter and into said probe;
   an eductor adjacent said second end of said probe for mixing the sample with a dilution gas; and
   a second heater for heating said eductor to maintain the sample gas at a temperature above its dew point as it passes through said eductor.

2. Apparatus, as claimed in claim 1, further including:
   a second cylindrical filter of slightly greater diameter than said probe, said second filter having a closed end and an open end and being positioned over said first end of said probe, but spaced therefrom.

3. Apparatus, as claimed in claim 2, wherein:
   said second filter is sintered metal; and
   said first heater surrounds said second filter.

4. Apparatus, as claimed in claim 3, further including:
   a first protective shroud around said second filter and said first heater.

5. Apparatus, as claimed in claim 4, further including:
   a second protective cylindrical shroud extending around the remainder of said probe and attached to said second end thereof.

6. Apparatus, as claimed in claim 5, further including:
   a third cylindrical shroud attached to and extending from said second shroud to protect fluid and the electrical lines connected to said probe.

7. Apparatus, as claimed in claim 2, wherein said sample drawing means includes:

a second eductor through which a gas passes;

means providing fluid communication from the space between said second filter and said first end of said probe to said second eductor so that the low pressure created by the gas passing through said second eductor draws said sample gas through said second filter into said probe and into said second eductor.

8. Apparatus, as claimed in claim 7, further including:

a fluid line connected between said second eductor and the stack to convey the gasses from said second eductor back to the stack.

9. Apparatus, as claimed in claim 8, wherein:

the gas provided to said second eductor is the dilution gas.

10. Apparatus, as claimed in claim 1, further including:

a stack probe extending from said first end of said dilution probe positionable in a stack through which the stack gas to be sampled passes.

11. Apparatus, as claimed in claim 10, further including:

a flange connected to said stack probe for attaching said probe assembly to the stack.

12. Apparatus, as claimed in claim 1, further including:

means sensing the sample gas pressure in said dilution probe;

means sensing the pressure in said eductor; and a dilution control panel for sensing and regulating said sample gas pressure and said eductor pressure.

13. Apparatus, as claimed in claim 1, further including:

a first temperature sensing means positioned to sense the temperature of said sample at said second filter;

a second temperature sensing means positioned to sense the temperature of said sample at said eductor; and a heater controller assembly connected to said first and second heaters and said first and second temperature sensing means to control the respective heaters in response to the temperatures sensed by the respective temperature sensing means.

* * * * *